(12) United States Patent
LaVon et al.

(10) Patent No.: US 9,421,137 B2
(45) Date of Patent: Aug. 23, 2016

(54) DISPOSABLE ABSORBENT REFASTENABLE ARTICLES AND METHODS FOR MANUFACTURING THE SAME

(71) Applicant: The Procter & Gamble Company, Cincinnati, OH (US)

(72) Inventors: Gary Dean LaVon, Liberty Township, OH (US); Jacob Alan Barnhorst, Deerfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 164 days.

(21) Appl. No.: 13/929,900

(22) Filed: Jun. 28, 2013

(65) Prior Publication Data

US 2014/0005628 A1     Jan. 2, 2014

Related U.S. Application Data

(60) Provisional application No. 61/666,065, filed on Jun. 29, 2012.

(51) Int. Cl.
| | |
|---|---|
| *A61F 13/15* | (2006.01) |
| *A61F 13/64* | (2006.01) |
| *A61F 13/56* | (2006.01) |
| *A61F 13/496* | (2006.01) |

(52) U.S. Cl.
CPC ............. *A61F 13/64* (2013.01); *A61F 13/4963* (2013.01); *A61F 13/5655* (2013.01)

(58) Field of Classification Search
CPC . A61F 13/4963; A61F 13/5655; A61F 13/64; A61F 13/49061
See application file for complete search history.

(56) References Cited

U.S. PATENT DOCUMENTS

| | | | |
|---|---|---|---|
| 6,579,275 B1 | 6/2003 | Pozniak | |
| 7,708,857 B2 | 5/2010 | Ukegawa | |
| 8,012,296 B2 | 9/2011 | Ukegawa | |
| 8,235,964 B2 | 8/2012 | Perneborn | |
| 8,287,512 B2 | 10/2012 | Gabriele | |
| 2003/0018315 A1* | 1/2003 | Popp | A61F 13/5622 604/386 |
| 2003/0078558 A1 | 4/2003 | Karami et al. | |
| 2003/0167049 A1 | 9/2003 | Gibbs | |
| 2006/0108054 A1* | 5/2006 | Ukegawa | 156/160 |
| 2010/0292663 A1 | 11/2010 | LaVon et al. | |
| 2012/0070254 A1* | 3/2012 | Hamada | 414/225.01 |
| 2014/0005020 A1 | 1/2014 | LaVon | |
| 2014/0276525 A1* | 9/2014 | LaVon et al. | 604/391 |

FOREIGN PATENT DOCUMENTS

WO   WO-2011/091110   7/2011

OTHER PUBLICATIONS

Written Report and International Search Report, PCT/US2013/048472, date of mailing Sep. 27, 2013.
All Office Actions, Responses and Claims for U.S. Appl. No. 13/929,970.

* cited by examiner

*Primary Examiner* — Bradley Philips
(74) *Attorney, Agent, or Firm* — Richard L. Alexander

(57) ABSTRACT

Absorbent articles of the disclosure may comprise first and second belt webs, a fastening tab member comprising first and second fastening elements, first and second mating fastening elements, and laterally opposing permanent side seams directly or refastenably joining the first and second belt webs. The fastening tab member may be joined to the first and second fastening elements. And, the absorbent article may be packaged in refastenably closed form.

11 Claims, 26 Drawing Sheets

DISPOSABLE ABSORBENT REFASTENABLE ARTICLES AND METHODS FOR MANUFACTURING THE SAME

CROSS REFERENCE TO RELATED APPLICATION

This application claims the benefit of U.S. Provisional Application No. 61/666,065, filed Jun. 29, 2012, the substance of which is incorporated herein by reference.

BACKGROUND

Currently, disposable absorbent pants are manufactured and marketed for wear by toddlers and young children who are not yet toilet trained, older children who are experiencing childhood enuresis, and adults suffering from incontinence. A disposable absorbent pant usually includes a central chassis having a core formed of absorbent material, enveloped between a liquid permeable, wearer-facing topsheet, and a liquid impermeable, outer- or garment-facing backsheet. The chassis is usually adapted to be positioned on the wearer such that it wraps between the wearer's legs and upwardly about the lower torso, such that the front and rear ends extend toward the wearer's waistline in the front and rear, respectively. The chassis is usually joined to a pair of stretch elements that each connects front and rear regions of the chassis on either side thereof, thereby forming a pant structure. In many current designs, the stretch elements are manufactured so as to be elastically extensible in the lateral direction, providing stretchability that eases donning, while providing a relatively snug and comfortable fit once donned.

In one configuration, an elasticized belt entirely encircles the wearer's waist and forms the waist edge about the entire pant. The central chassis may be joined to the elasticized belt, usually on the inside thereof, with its ends disposed at locations in the front and rear waist regions somewhat below the waist edges of the elasticized belt. This configuration is sometimes known as a "belt" or "balloon" configuration (hereinafter, "belt" configuration). An example of this type of configuration is currently manufactured and sold in Asia by The Procter & Gamble Company under the trademark PAMPERS, and also by Unicharm Corporation under the trademark MAMY POKO.

While both configurations have their advantages, in some circumstances a belt configuration may be deemed desirable. Among other advantages, because the encircling belt may be made elastically extensible in the lateral direction, considerable elastic stretch and contraction as well as targeted elastic profiles may be provided entirely about the wearer's waist.

For purposes of ease of use it may be desired that a pant have a refastenable feature for enabling ease of opening and reclosing of the belt-like structure. This may be accomplished by incorporating for example mechanical fastening elements into the structure of the absorbent article as part of the belt-like structure, the central chassis, other elements of the article and/or combinations thereof. The refastenable feature may help maintain and/or establish the leg openings and the waist opening. Although some currently manufactured belt configuration pants include refastenable features they may be considered to be too complex to produce—especially at high production speeds, and too complex to use. And, some may be considered to have a rough or unfinished appearance.

Therefore, the present disclosure reveals improvements to the structural design and process for making of disposable absorbent pants having a belt configuration comprising fastening components for forming a refastenable feature with increased manufacturability at high speeds.

DEFINITIONS

Figure 1:
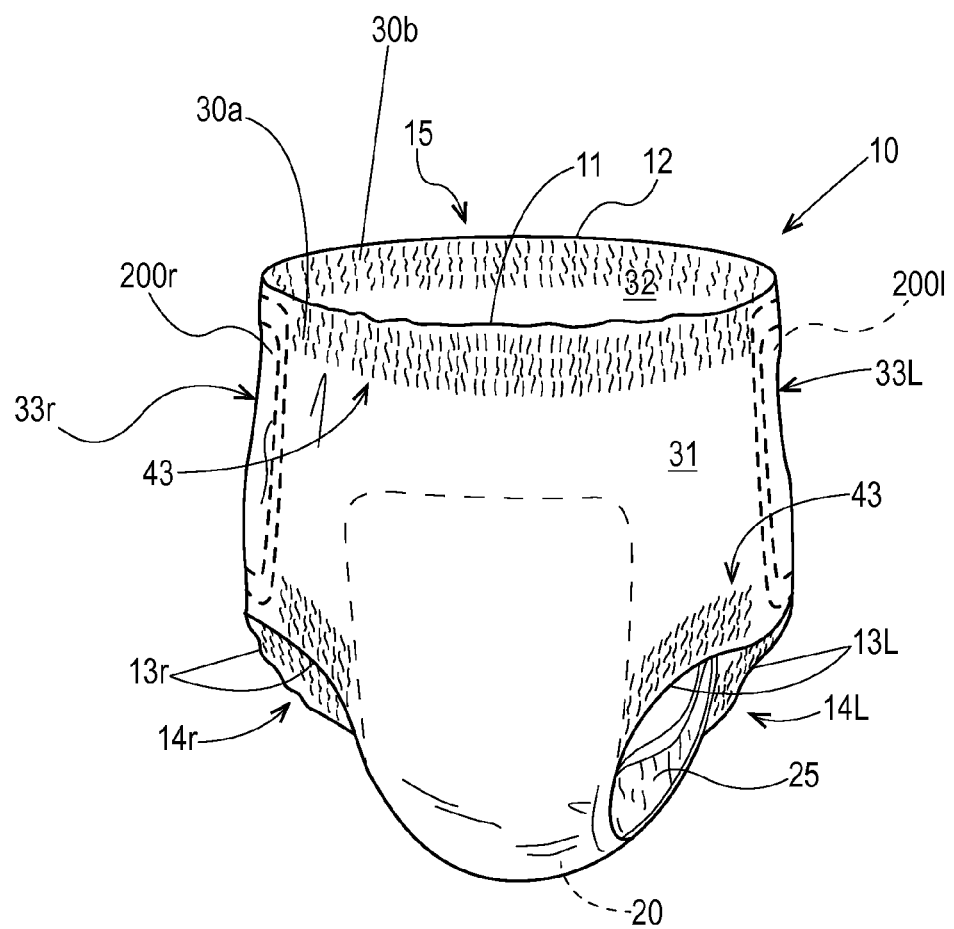
FIG. 1 is simplified perspective view of a disposable absorbent pant.

The term "fastening component" refers to the fastening elements that define an area of refastenable attachment. The fastening components enable refastening of the absorbent article to reconfigure the waist and leg openings into a closed configuration until the fastening components are separated. A fastening component may comprise of one or more refastenable fastening elements, e.g., hooks, loops, bulbs, mushrooms, arrowheads, balls on stems, buttons, snaps, refastenable cohesives, selective refastenable adhesives, etc. A fastening component may be opened and subsequently reclosed, reliably, without destroying the fastening component. A fastening component comprises those elements of a fastening system that form the area of attachment via direct surface-to-surface contact forming a refastenable closure. For the purpose of clarity, surface-to-surface contact encompasses contact between a surface of a hook material and a surface of a loop material, for example. For instance, a tab member joined to a backsheet would not be a fastening member as discussed. The fastening component may be the hooks or the loops that are joined to the tab and connect with the other fastening components or a portion of an absorbent article.

The term "initial waist opening circumference" refers to the circumference of a waist opening of the disposable training pant at the time the disposable training pant is placed in the package and, subsequently, when it is removed from the package by the consumer.

"Cross direction" (CD)—with respect to the making of a nonwoven web material, the nonwoven material itself, a laminate thereof, or an article in which the material is a component, refers to the direction along the material substantially perpendicular to the direction of forward travel of the material through the manufacturing line in which the material and/or article is manufactured.

As used herein, the term "elastic" or "elastomeric" refers to the property of an extensible material (or a composite of multiple materials) that can extend, without substantial rupture or breakage, to a strain of 100% in the Hysteresis Test, with a set less than or equal to 10% of the elongation as measured according to the Hysteresis Test. An elastic material is considered elastically extensible.

"Machine direction" (MD)—with respect to the making of a nonwoven web material, the nonwoven material itself, a laminate thereof, or an article in which the material is a component, refers to the direction along the material substantially parallel to the direction of forward travel of the material through the manufacturing line in which the material and/or article is manufactured.

"Lateral"—with respect to a pant and its wearer, refers to the direction generally perpendicular with the wearer's standing height, or the horizontal direction when the wearer is standing. "Lateral" is also the direction generally perpendicular to a line extending from the midpoint of the front waist edge to the midpoint of the rear waist edge.

"Longitudinal"—with respect to a pant and its wearer, refers to the direction generally parallel with the wearer's standing height, or the vertical direction when the wearer is standing. "Longitudinal" is also the direction generally parallel to a line extending from the midpoint of the front waist edge to the midpoint of the rear waist edge.

The term "pant" (also referred to as "disposable training pant," "training pant," and "pull-on pant-type diaper") refers to disposable absorbent articles having a continuous perimeter waist opening and continuous perimeter leg openings designed for infant, child, or adult wearers (hereafter "wearer"). A pant may be configured with a continuous or closed waist opening and at least one continuous or closed leg opening prior to the pant being applied to the wearer. A pant may be pre-formed by any suitable technique including, but not limited to, joining together portions of the absorbent article using any refastenable and/or permanent closure member(s) (e.g., seams, heat bonds, pressure welds, adhesives, cohesive bonds, mechanical fasteners, etc.). A pant may be preformed anywhere along its circumference in the waist region (e.g., side fastened, front waist fastened, rear waist fastened). Example pants and pant configurations are disclosed in U.S. Pat. Nos. 5,246,433, 5,569,234, 6,120,487, 6,120,489, 4,940,464, 5,092,861, 5,897,545, 5,957,908, and U.S. Pat. Publ. No. 2003/0233082.

The term "secondary waist opening circumference" refers to the circumference of the waist opening of the pant after the initial waist opening circumference has been broken and the pant has been refastened.

The term "side edge seam" refers to a given side edge wherein a portion of the side edge, or region adjacent the side edge, in the front waist region is joined to a portion of the same side edge, or region adjacent the side edge, in the rear waist region to define closed, encircled leg openings and a closed waist opening.

FIG. 1 is a general simplified perspective depiction of a disposable absorbent pant 10 having a belt configuration. Pant 10 may include a central chassis 20 and a elasticized belt 30. Elasticized belt 30 may be elastically extensible in the lateral direction, providing elastic stretchability for ease of donning, and a snug and comfortable fit following donning. Central chassis 20 may include a wearer-facing, liquid permeable topsheet (not specifically shown in FIG. 1), an outer- or garment-facing backsheet (not specifically shown in FIG. 1) and an absorbent core (not specifically shown in FIG. 1) sandwiched or enveloped between the topsheet and backsheet. A pair of laterally opposing, longitudinally extending barrier cuffs 25 also may be included with the central chassis in a crotch region thereof, disposed adjacent to the topsheet. Generally the central chassis and barrier cuffs may have any construction and components, including leg cuff structures, suitable for disposable diapers, training pants, and adult incontinence pants, such as, but not limited to, those described in U.S. provisional patent application No. 61/480, 663 and application(s) claiming priority thereto. Elasticized belt 30 may have a front portion 31 and a rear portion 32. Front and rear portions 31, 32 may be joined together at respective left and right side edge seams 33l, 33r. Elasticized belt 30 may form front and rear waist edges 11, 12 defining waist opening 15, and at least portions of left and right leg opening edges 13l, 13r of the pant 10. The disposable absorbent pant 10, and more particularly, the elasticized belt 30 may comprise fastening components 200l and 200r for creating a refastenable feature.

Figure 2:
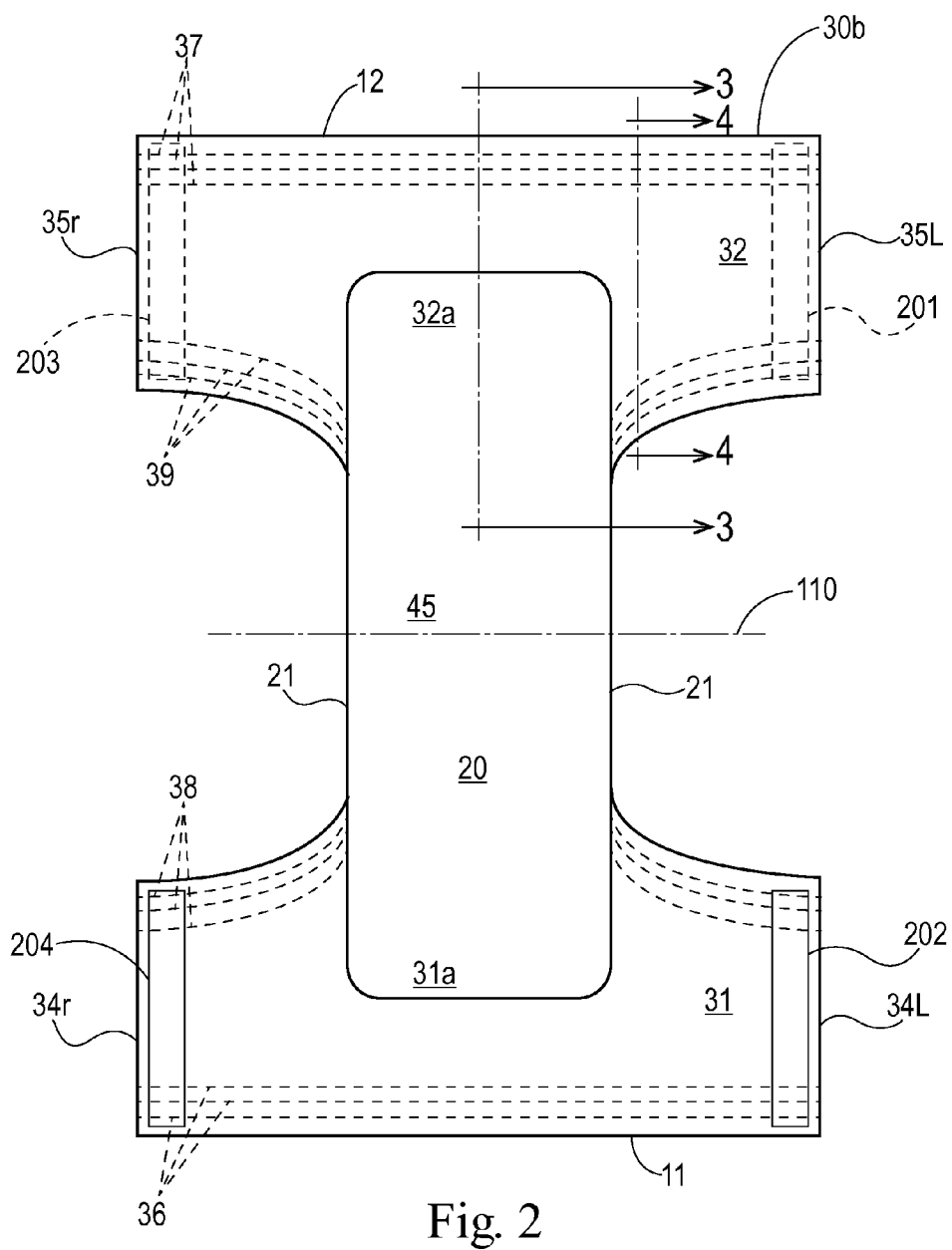
FIG. 2 is a simplified plan view of a precursor structure of a disposable absorbent pant, shown with inner or wearer-facing surfaces upward.

FIG. 2 is a simplified plan view of the precursor structure of the pant 10 shown in FIG. 1, shown prior to joining of front and rear portions 31, 32 along their respective side edges 34l, 35l and 34r, 35r. Front region 31a, including front portion 31, and rear region 32a, including rear portion 32, may each include anywhere from 25 percent to 40 percent of the overall longitudinal length of the precursor structure; correspondingly, a crotch region 45 may include anywhere from 20 percent to 50 percent of the overall longitudinal length of the precursor structure, with at least a portion thereof lying at lateral axis no. To form pant 10, the precursor structure may be folded along lateral axis no to bring front and rear regions 31a, 32a, and front and rear portions 31, 32 together such that their side edges 34l, 35l and 34r, 35r, respectively, may be joined at side edge seams 33l, 33r (as shown in FIG. 1). The embodiment shown in FIG. 2 comprises fastening elements 201-204 that may be refastenably joined together. Particularly, fastening elements 201 and 203 may be hook elements that join with fastening elements 202 and 204, respectively. Fastening elements 201 and 203 are shown on an exterior surface of the elasticized belt 30, but they may also be placed on an interior surface of the elasticized belt 30. Fastening elements 202 and 204 may be a discrete member of loop elements or may be an area of loop elements that is part of a nonwoven sheet lining the interior (as shown) or exterior of the elasticized belt. In another embodiment, fastening elements 201 and 203 may be loop elements and fastening elements 202 and 204 may be hook elements.

It is understood that when the fastening elements 201-204 mate interior surface to interior surface of the elasticized belt 30, a flange seam is formed. But, when the fastening elements 201-204 mate interior surface to exterior surface of the elasticized belt 30, an overlap seam is formed, as illustrated in FIG. 1. The fastening elements 201-204, first and second fastening elements 202 and 204 and first and second mating fastening elements 201 and 203, may be fastened during the manufacturing process and/or fastened in the package prior to use by the wearer or caregiver (i.e., the pant may be sold in "closed form"). Alternatively, the pant may be sold in "open form," where the fastening elements 201-204 are present but are not joined in the package.

Still referring to FIG. 2, one or both of front and rear portions 31, 32 may include at least a first elastic member 36, 37 disposed nearer the waist edges 11, 12 and at least a second elastic member 38, 39, disposed nearer the leg opening edges 13l, 13r. As suggested in FIG. 2, one or a plurality of waist elastic members 36, 37 may be disposed in a substantially straight lateral orientation, and one or a plurality of leg elastic members 38, 39 may be disposed along curvilinear paths to provide hoopwise elastic stretch about the leg openings 13l, 13r (as shown in FIG. 1). For purposes of manufacturing a pant having a neat appearance as will be described below, it may be desired that leg elastic members 38, 39 terminate proximate the respective longitudinal edges 21 of chassis 20. For purposes herein, where used to describe a positional relationship between two features, "proximate" is intended to mean within 2.0 cm of the identified features.

Elastic members 36, 37, 38 and 39 may be in the form of film or sections or strips thereof, strips, ribbons, bands, scrims, elastic nonwovens or strands of circular or any other cross-section, formed in any configuration of any elastomeric material such as described in, for example, co-pending U.S. application Ser. Nos. 11/478,386 and 13/331,695, and U.S. Pat. No. 6,626,879. A suitable example is LYCRA HYFIT strands, a product of Invista, Wichita, Kans.

Figure 3A:
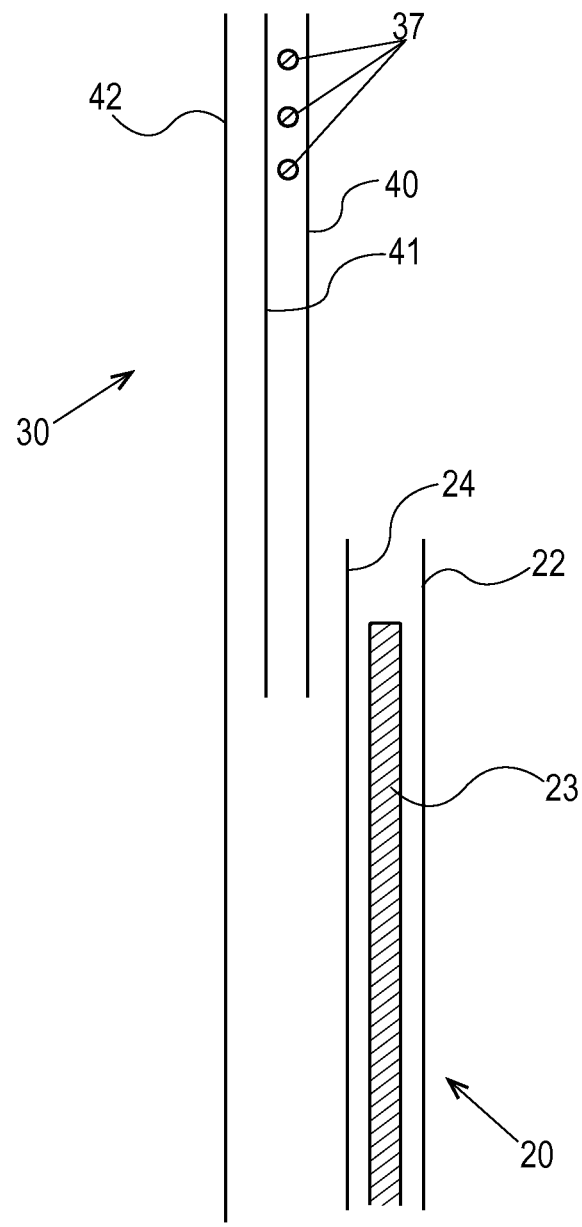
FIG. 3A is a simplified, schematic cross-section view taken through line 3-3 of FIG. 2, in one example of a possible configuration.
Figure 3B:
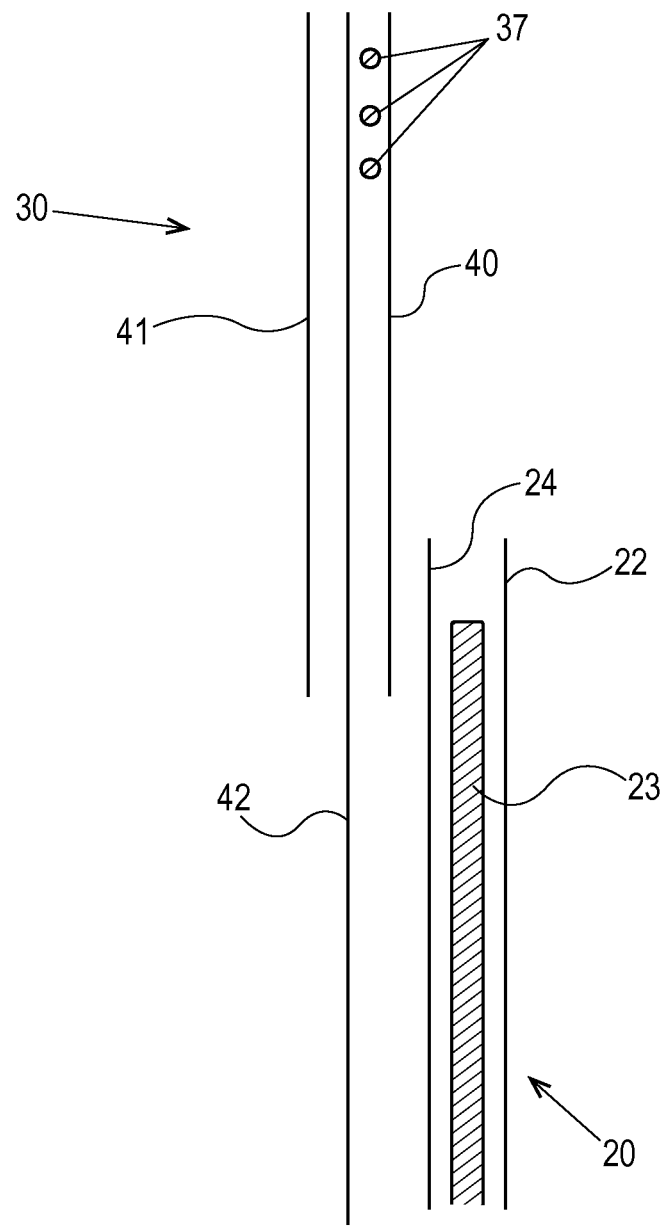
FIG. 3B is a simplified, schematic cross-section view taken through line 3-3 of FIG. 2, in another example of a possible configuration.
Figure 3C:
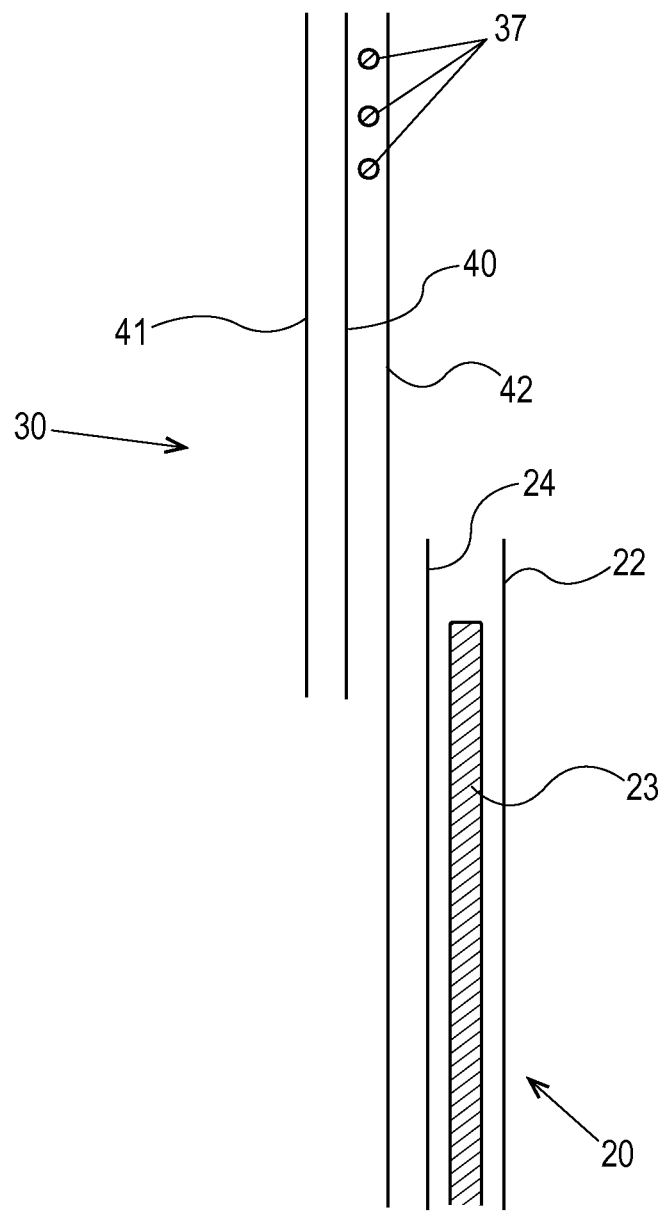
FIG. 3C is a simplified, schematic cross-section view taken through line 3-3 of FIG. 2, in another example of a possible configuration.

FIGS. 3A-3C are examples of potential longitudinal cross-sections taken at line 3-3 through the rear portion 32 of the elasticized belt and rear region of the pant as shown in FIG. 2, depicting features in three possible configurations. It can be appreciated that in each of these particular examples, the cross-section may substantially mirror a cross-section taken through the front portion 31 of the elasticized belt and the front region of the pant.

Figure 4A:
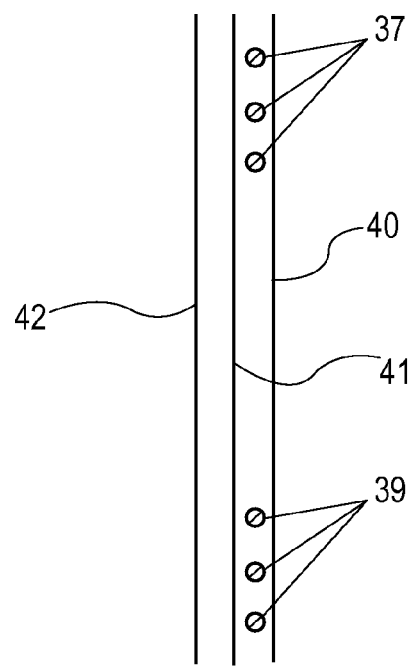
FIGS. 4A-4K are simplified, schematic cross-section views taken through line 4-4 of FIG. 2, in various examples of possible configurations.
Figure 4B:
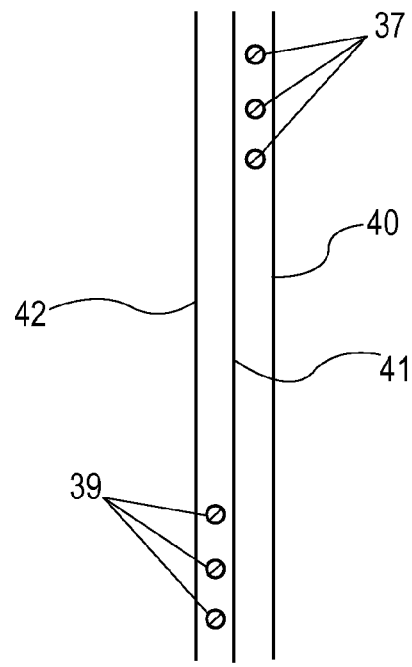
Figure 4C:
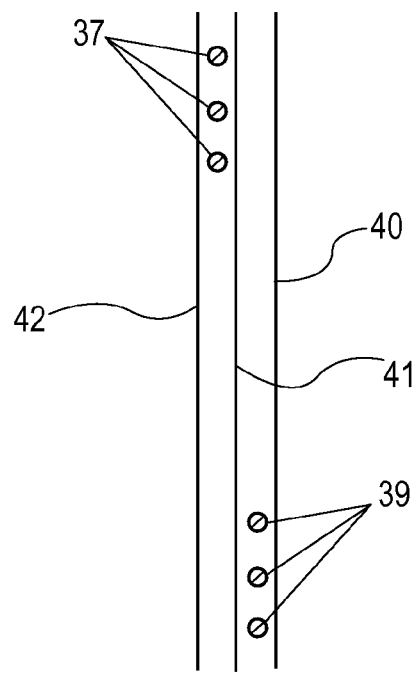
Figure 4D:
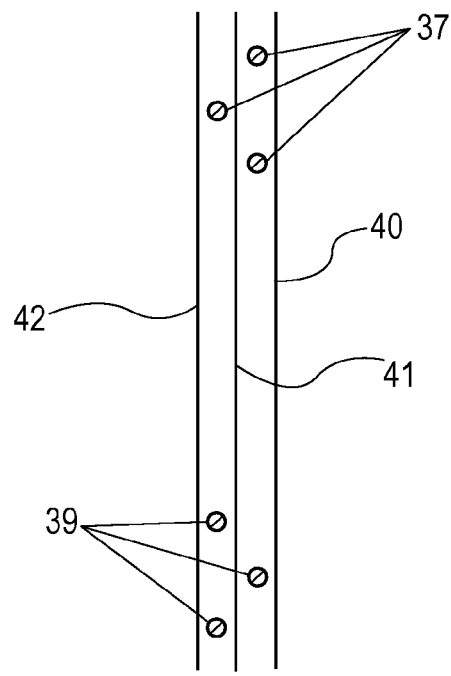
Figure 4E:
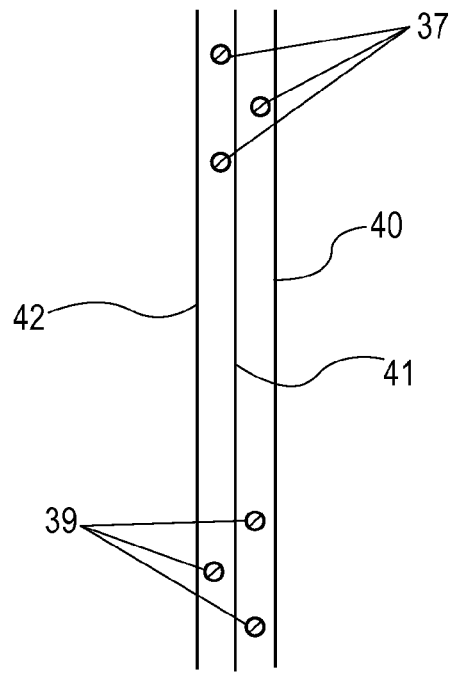
Figure 4F:
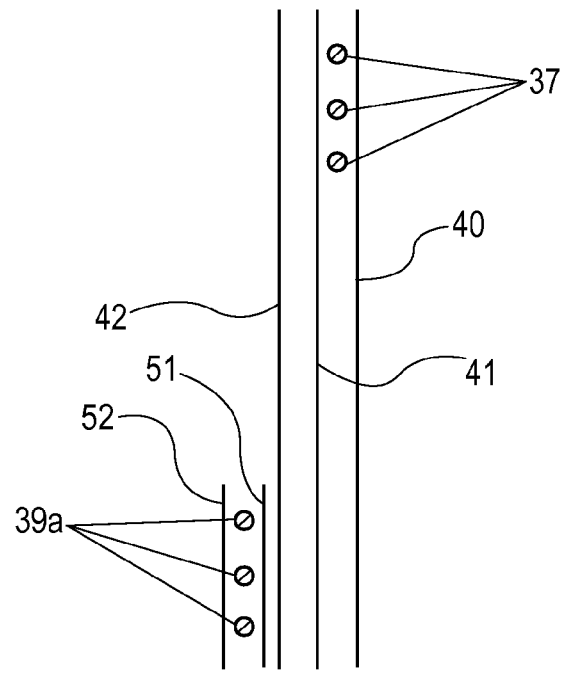
Figure 4G:
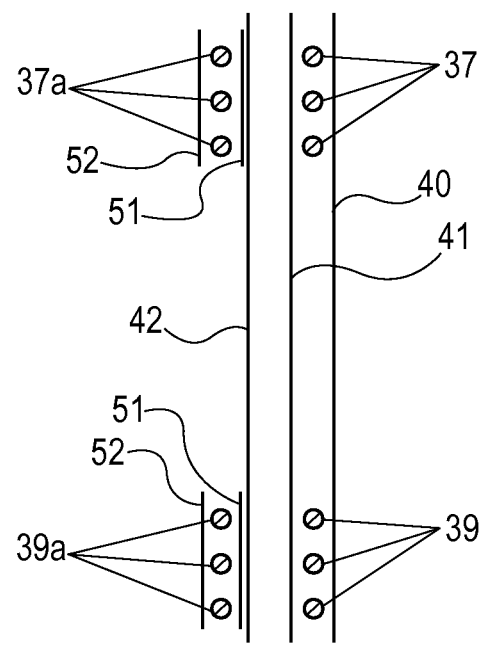
Figure 4H:
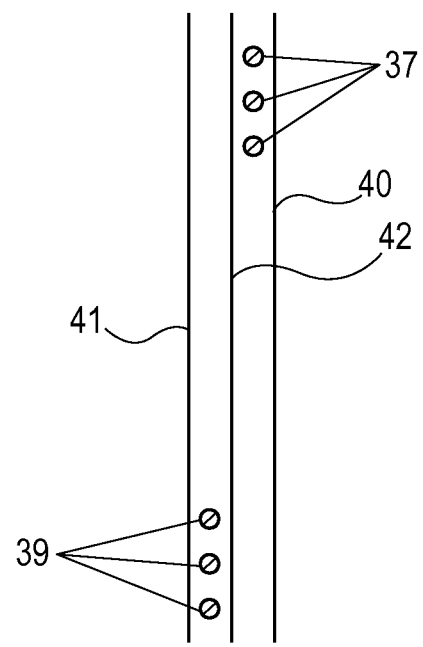
Figure 4I:
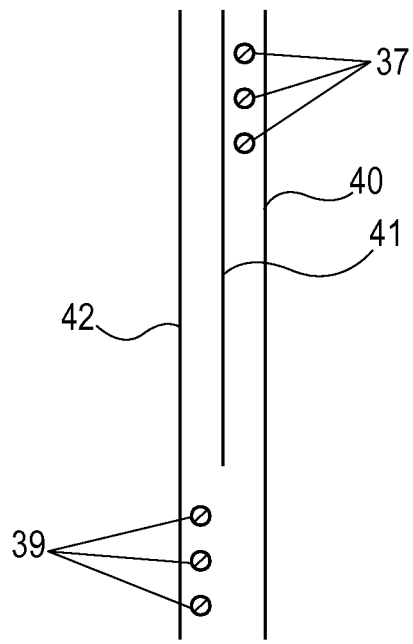
Figure 4J:
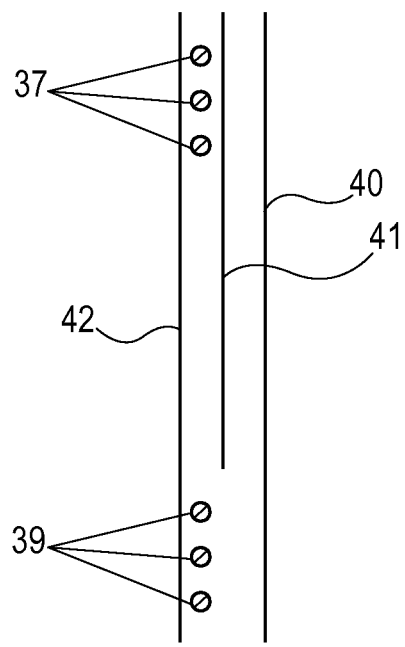
Figure 4K:
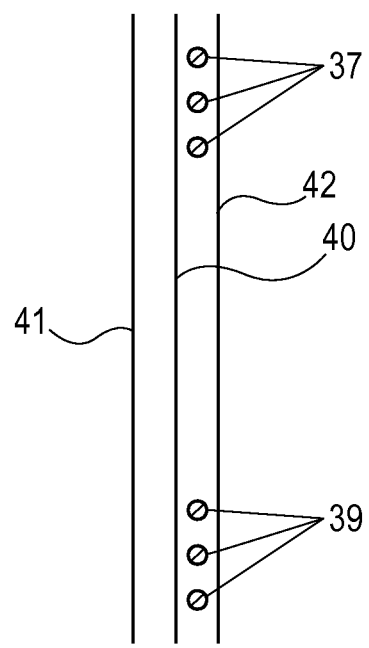
Figure 5A:
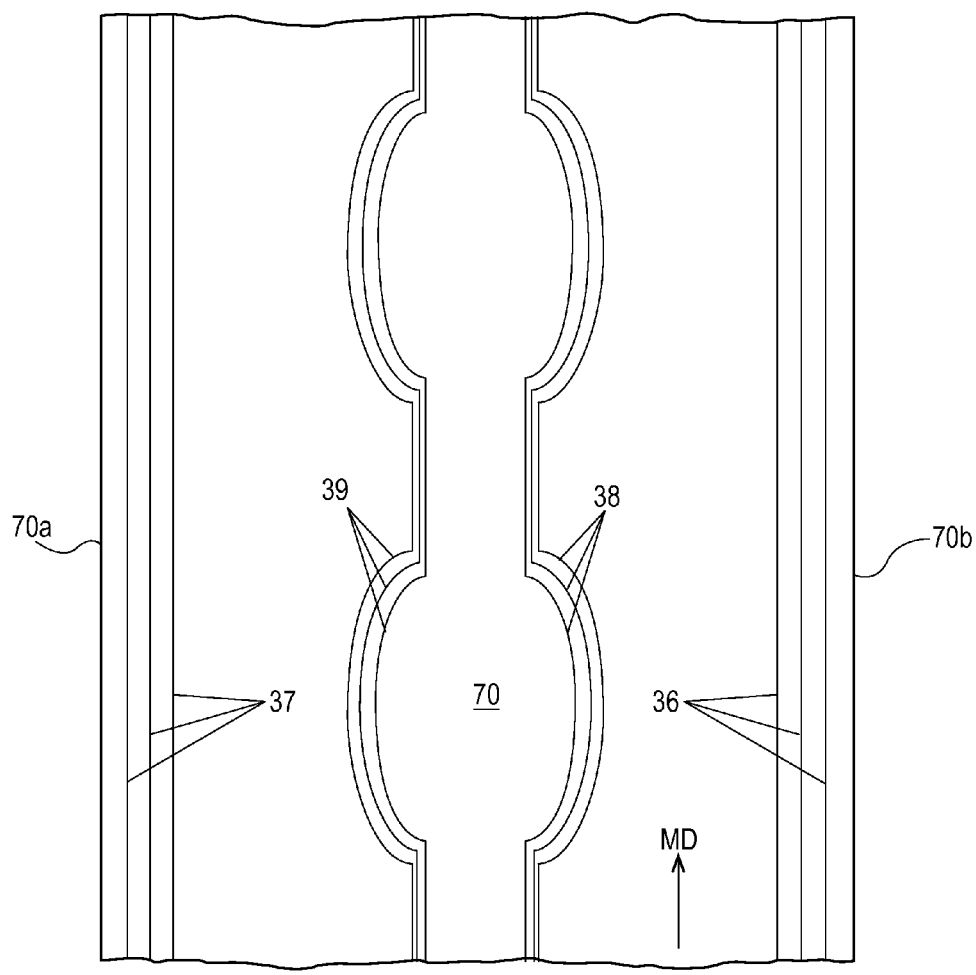
FIG. 5A is a plan view of a portion of a nonwoven web with applied elastic members.
Figure 5B:
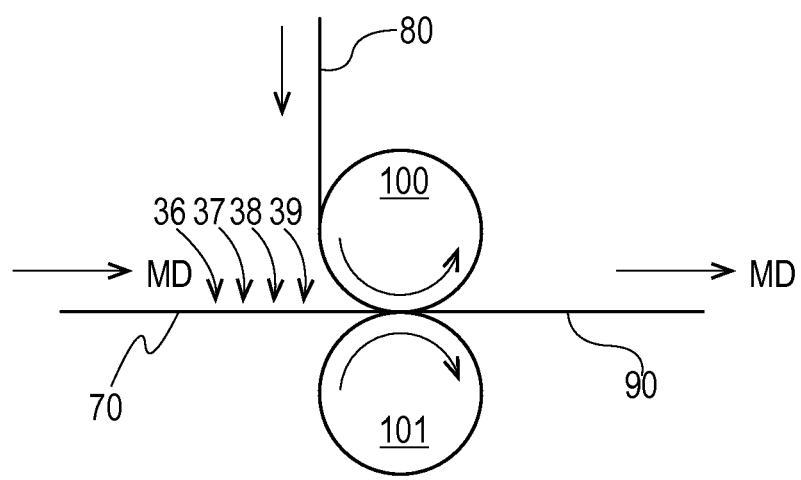
FIG. 5B is a simplified schematic view of equipment and components for manufacturing a laminate, shown along a cross-direction view.
Figure 6A:
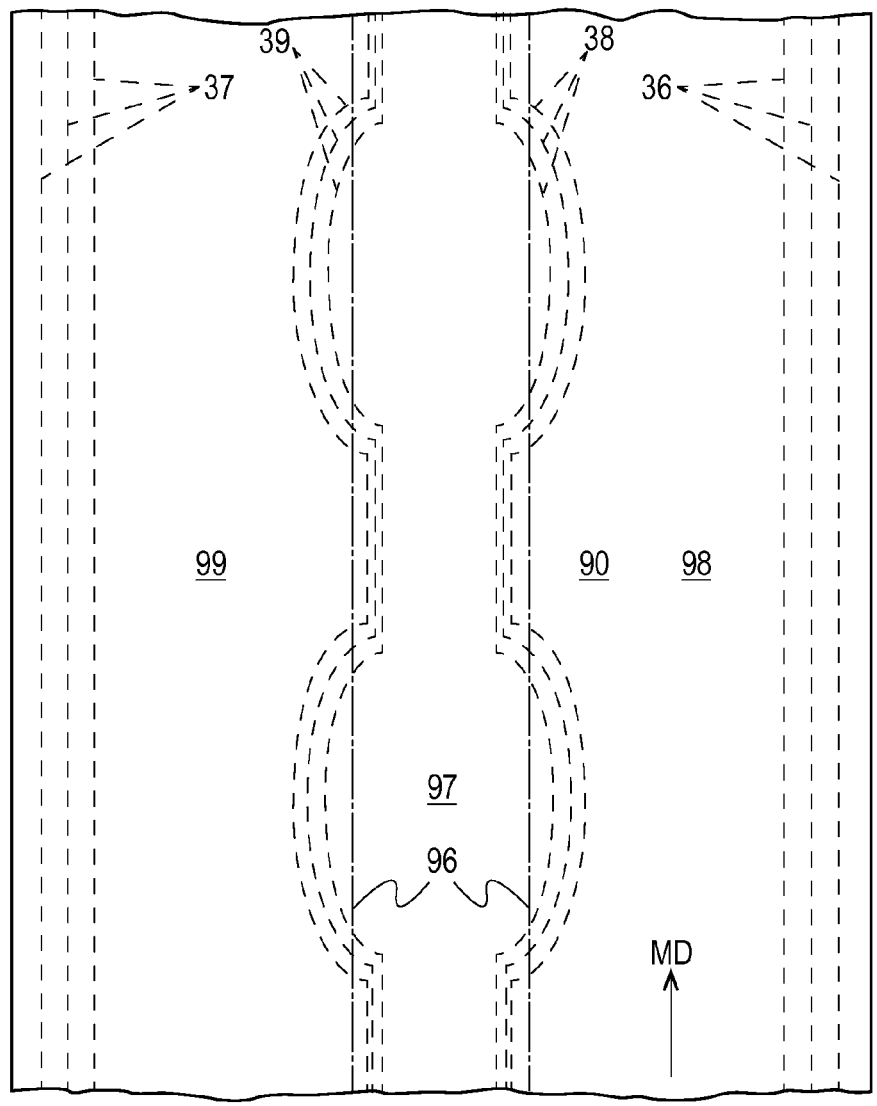
FIG. 6A is a plan view of a portion of a multilayer web shown with cut lines.
Figure 6B:
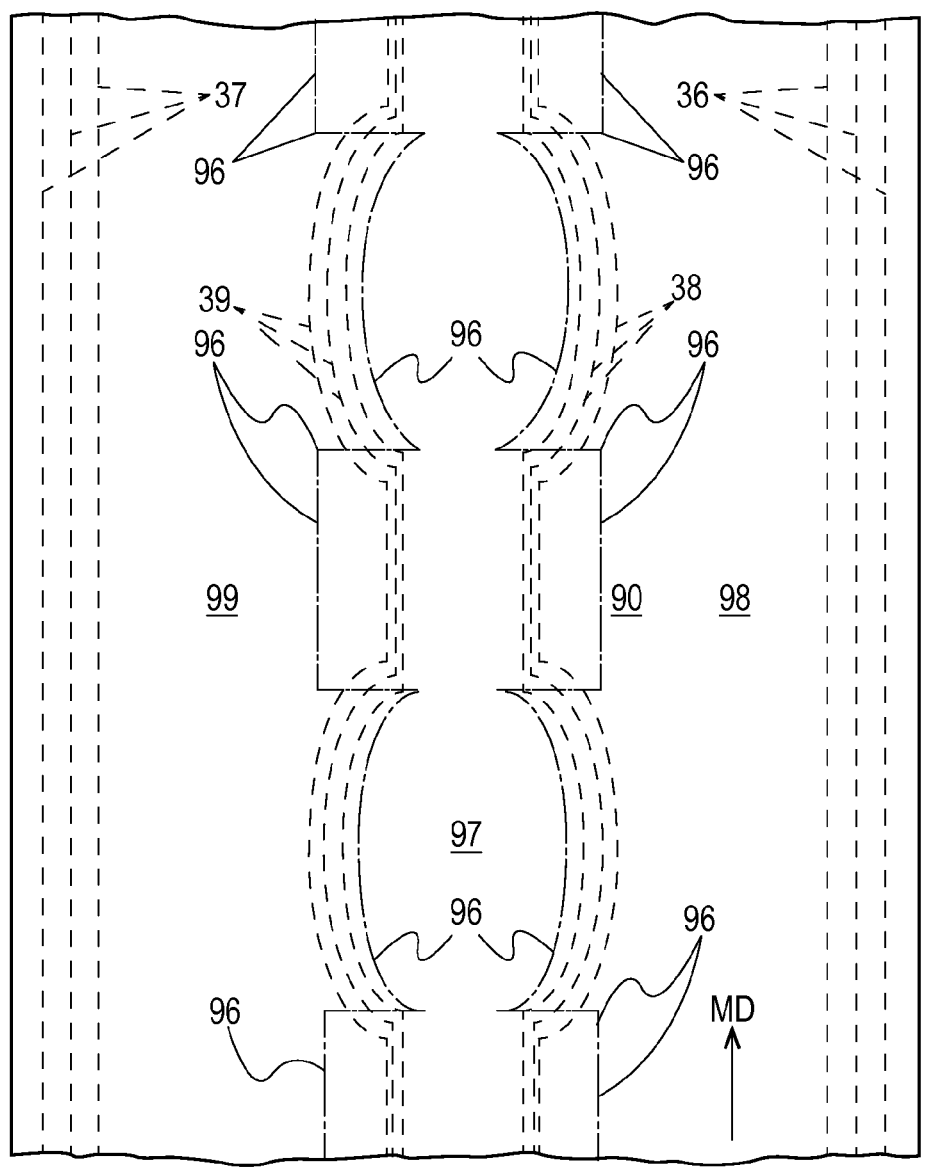
FIG. 6B is a plan view of a portion of a multilayer web shown with cut lines in an alternative configuration.
Figure 6C:
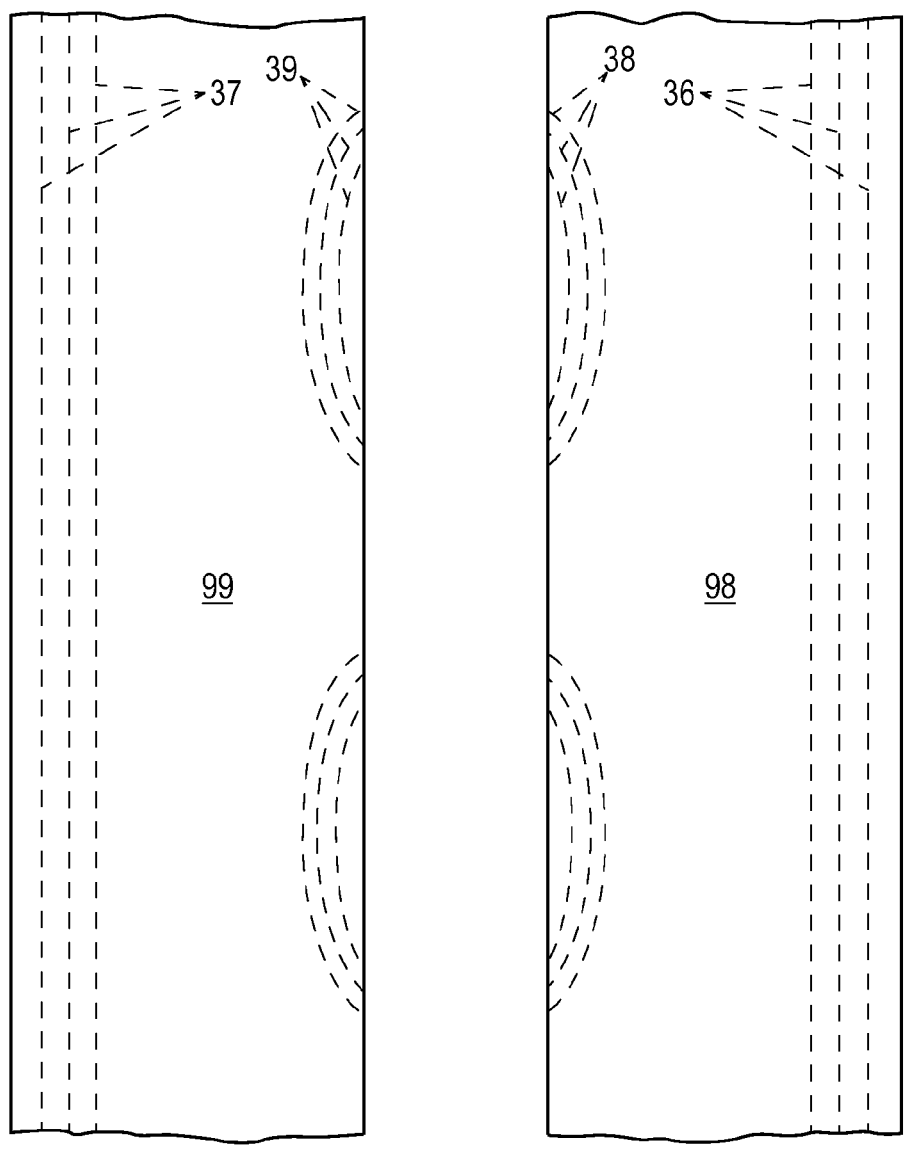
FIG. 6C is a plan view of portions of the multilayer web as shown in FIG. 6A, with a middle section severed away.
Figure 6D:
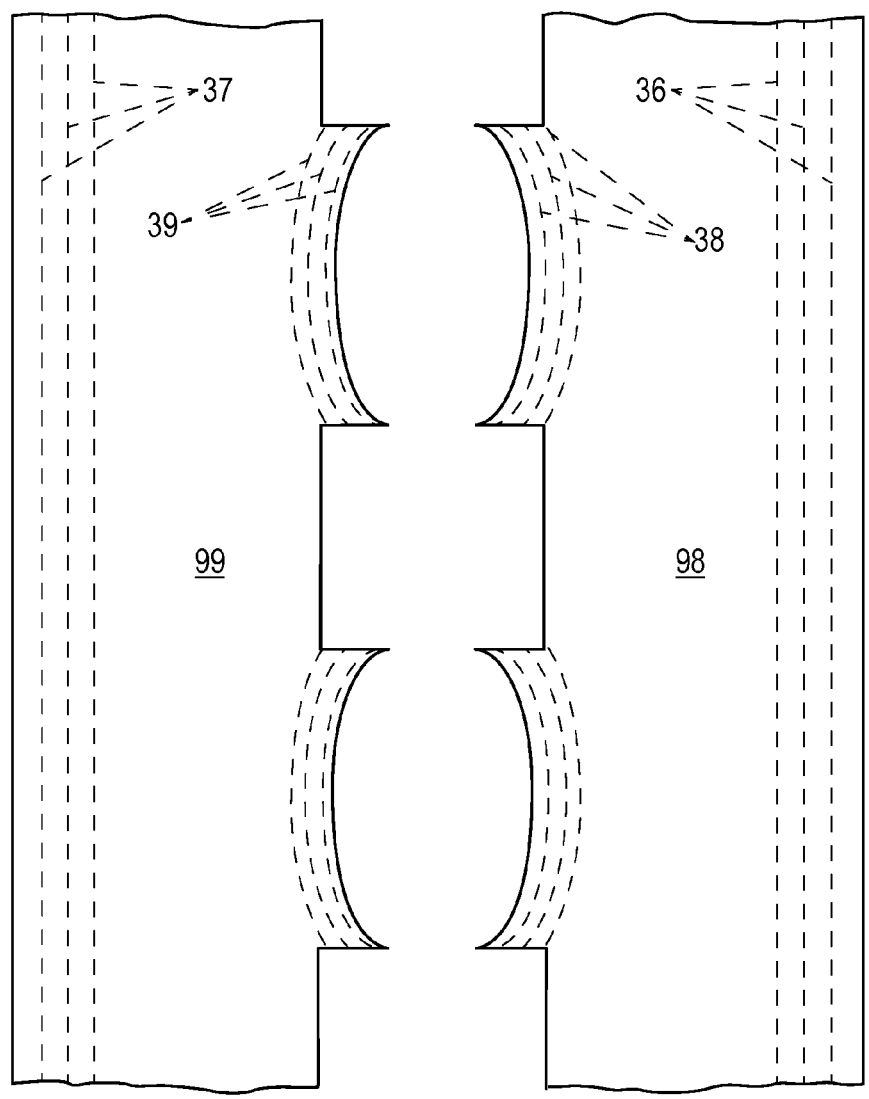
FIG. 6D is a plan view of portions of the multilayer web as shown in FIG. 6B, with a middle section severed away.
Figure 6E:
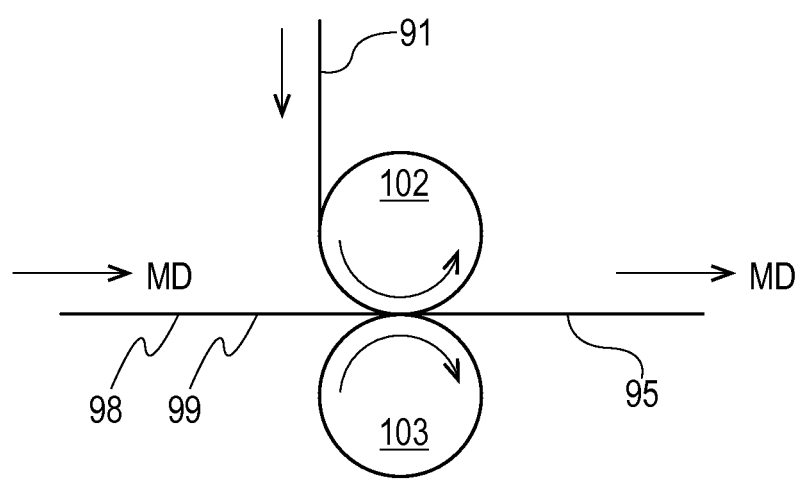
FIG. 6E is a simplified schematic view of equipment and components for manufacturing a laminate, shown along a cross-direction view.

FIG. 4A is an example of a potential longitudinal cross-section taken at line 4-4 through the rear portion 32 of the elasticized belt and rear region of the pant as shown in FIG. 2, depicting features in one configuration. It can be appreciated that this cross-section may also be a substantial mirror image of a cross-section taken through the front portion 31 of the elasticized belt and the front region of the pant. Elasticized belt 30 where shown in FIG. 4A has the same layers and components as those depicted in FIG. 3A, but with the addition of leg elastic members 39 and without the chassis components, as a result of the location of the cross-section. As suggested in FIG. 2, leg elastic members 39 may terminate proximate the longitudinal edges 21 of central chassis 20; thus, they do not appear in FIGS. 3A and 3B.

Referring to FIGS. 3A-3C, chassis 20 may have liquid permeable topsheet 22 forming at least a portion of its inner, wearer-facing surface. Topsheet 22 may be formed of a non-woven web material which is preferably soft and compatible with sensitive skin, and may be formed of and have any of the features of topsheets used in disposable diapers, training pants and inserts including those described in, for example, co-pending U.S. application Ser. No. 12/841,553. Chassis 20 may also have an outward-facing backsheet 24, which may be liquid impermeable. Backsheet 24 may be formed of and have any of the features of backsheets used in disposable diapers and training pants including those described in, for example, the co-pending U.S. patent application referenced immediately above. Chassis 20 may also have an absorbent core 23 disposed between topsheet 22 and backsheet 24. Absorbent core 23 may include one or more absorbent acquisition, distribution and storage material layers and/or components; it may be formed of and have any of the features of absorbent cores used in disposable diapers and training pants including those described in, for example, the co-pending U.S. patent application referenced immediately above.

As suggested in FIGS. 3A-3C, chassis 20 may be affixed to a elasticized belt 30, to the inner, wearer-facing side thereof, or alternatively, to the outer, garment-facing surface thereof. Chassis 20 may be joined to the elasticized belt 30 by adhesive, by thermal bonds/welds, mechanical fasteners or a combination thereof.

Referring to FIGS. 3A and 4A, elasticized belt 30 may have a first belt layer 40, which may be formed of a suitable nonwoven web material. Since the first belt layer may come into direct contact with the wearer's skin, it may be deemed preferable to select a nonwoven web material for the layer that is soft, comfortable and relatively breathable/vapor permeable. One or more waist elastic members 37 may be disposed between first belt layer 40 and a second belt layer 41. Second belt layer 41 may be formed of the same, similar or differing nonwoven web material as first belt layer 40. First belt layer 40 and second belt layer 41 may be bonded together by adhesive, a pattern of thermal bonds or a combination thereof, such that first belt layer 40 and second belt layer 41 form a laminate, with the one or more waist elastic members 37 sandwiched and affixed therebetween. Similarly, referring to FIG. 4A, the one or more leg elastic members 39 may be affixed and sandwiched between first belt layer 40 and second belt layer 41. In an alternative embodiment belt layer 41 may be formed of an elastomeric web material such as an elastomeric nonwoven or an elastic film when belt layer 41 is disposed between belt layer 40 and outer cover layer 42. The belt layer 41 when formed of an elastomeric web material may be prestrained prior to joining the belt layer 41 to the other layers of the article or it may be joined in a relaxed state and subsequently mechanically strained. In such an alternative embodiment the one or more waist elastic members and the one or more leg elastic members may be disposed between the belt layers. Alternative elastic member placements are shown in FIGS. 4a-4k.

Figure 8:
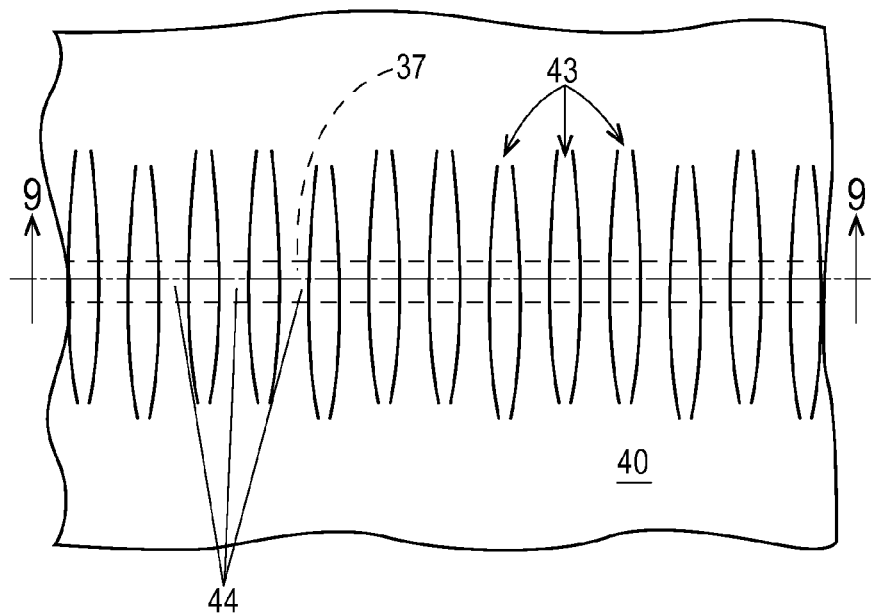
FIG. 8 is a plan view of a portion of a multilayer web including two nonwoven layers and a pre-strained elastic member, with formations of shirrs along the elastic member in the nonwoven layers.
Figure 9:
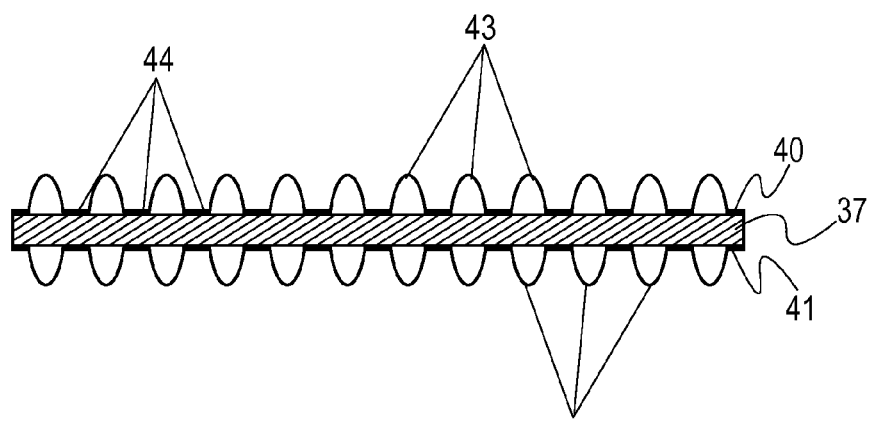
FIG. 9 is a cross-section view along line 9-9 in FIG. 8.

Referring to FIGS. 8 and 9, during manufacture, the one or more waist elastic members 37 may be pre-strained along the direction of their lengths or longer dimensions, before they are affixed between the layers, for example first belt layer 40 and second belt layer 41, such that, upon completion of manufacture and subsequent relaxation, contraction of elastic members 37 will induce a pattern of wrinkles, pleats, corrugations or rugosities (hereinafter, "shirrs") 43 in first belt layer 40 and second belt layer 41. The shirrs 43 are formed of material that gathers about the elastic members as they contract, and the gathered material serves to accommodate stretching and contraction of the elasticized belt 30. The shirrs 43 are oriented along fold or bending lines roughly transverse or perpendicular to the direction of lateral contraction of the elastic members 37. The shirrs may also provide a three dimensional surface which when formed by a nonwoven material may enhance engagement of fastening components such as hooks into one of the belt layers. Alternatively, it may be beneficial to eliminate the shirrs and contraction in the area of attachment (e.g., area comprising loops) or area of fastening (e.g., area comprising hooks) of the fastening components 200.

Similarly, the one or more leg elastic members 39 may be pre-strained along their paths of placement (which, as noted, may be curvilinear) during manufacture before they are affixed between the layers, such that, upon completion of manufacture and subsequent relaxation, contraction of elastic members 39 will induce a pattern of shirrs in first belt layer 40 and second belt layer 41. These shirrs are also formed of material that gathers about the elastic members as they contract, and serve to accommodate stretching and contraction of the elasticized belt 30 about the leg openings. The shirrs are oriented along fold or wrinkle lines roughly transverse or perpendicular to the direction of contraction of the elastic members 39.

Still referring to FIGS. 8 and 9, patterns of deposits of adhesive may be applied to either of the layers 40, 41, and/or to the elastic members 37, 39 to adhere the layers to the elastic members 37 at adhered portions 44, in regular patterns and/or intervals, so that the shirrs formed upon relaxation and contraction of elastic members 37, 39 are somewhat uniform, evenly distributed and neat in appearance. The frequency and size of the shirrs can also be adjusted by adjusting the pattern of attachment of the elastics to the belt layers or the belt layers to each other or combinations thereof. The frequency and size of the shirrs may be adjusted to coordinate functionally with the fastening component(s) 200, for example finer shirrs may be more effective with smaller hooks or denser patterns of hook-type fastening components while larger shirrs may be more effective with larger hooks or less dense patterns of hook-type fastening components.

One or more of elastic members 36, 37, 38 and 39 may be varied from one or more of the others in various ways to impart differing stretch and force characteristics. For example, it may be desired that curvilinear leg elastic members exert greater or less tension about the leg openings than exists about the waist opening during wear, for fit snugness about these openings that differ according to specific design circumstances. One or more of the elastic members 36, 37, 38 and 39 may be selected and/or configured so as to differ from one or more of the others in a respect selected from number of elastic strands or bands, cross-sectional size of elastic strands or bands, cross-sectional shape of elastic strands or bands, chemical composition of material from which elastic strands or bands are formed, amount of pre-strain imparted to the elastic strands or bands during manufacture of the pant, and combinations thereof.

In addition to the waist elastic members 36, 37 and curvilinear leg elastic members 38, 39, additional elastic members (not shown) may be included longitudinally therebetween, to impart additional stretch, contraction and load/force bearing capability to the elasticized belt, in the same manner as such capability is imparted by the waist and leg elastic members. The additional elastic members may be disposed between the same pairs of layers as any of elastic members 36, 37, 38 and 39, or may be disposed between differing pairs of layers, and may be disposed in alternating locations between differing pairs of layers as described above. In certain embodiments wherein one or more of the elastic members are curved or angled it may be beneficial to angle the fastening components to cooperate functionally with the angle or curvature of the elastic members.

Some examples described above, as well as other examples not expressly described, may also be advantageous because they may lend themselves to relatively efficient manufacture.

Figure 11:
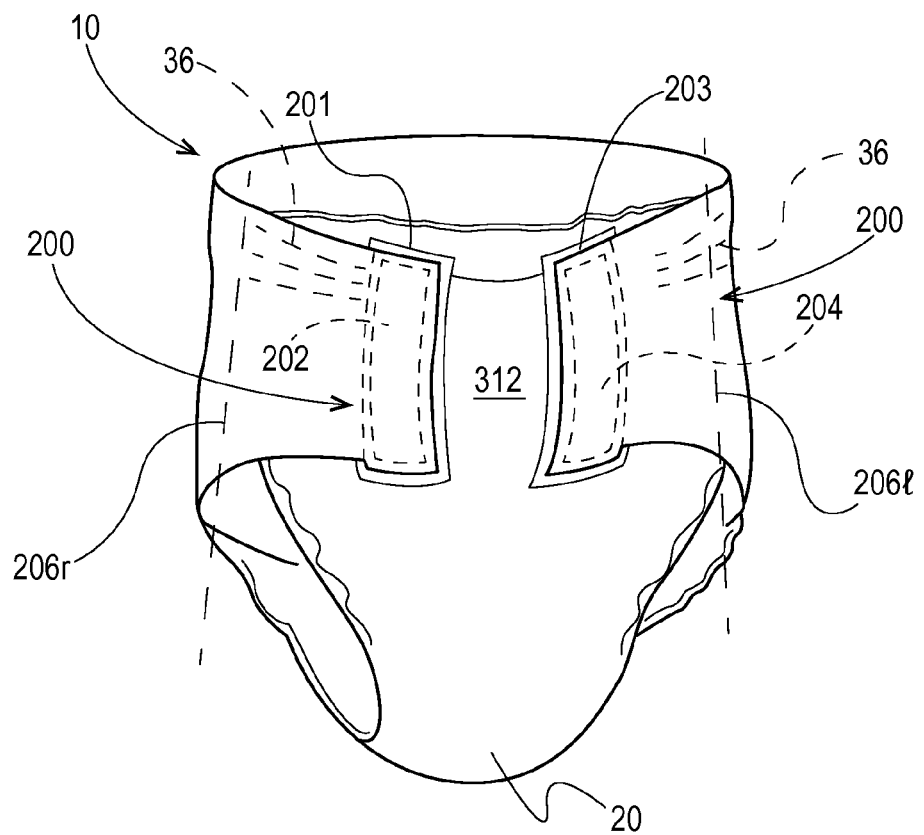
FIG. 11 is simplified perspective view of a disposable absorbent pant.

Referring to FIG. 11, in one embodiment, the fastening elements 201-204 may, when joined to form the leg and waist openings 14 and 15, respectively, be disposed or formed within the front region 31a of the pant 10 to improve access to the fastening components 200. When the fastening elements are joined and the leg and waist openings are formed, the front region 31a may be considered the area of the pant 10 forward of each of the hip axis 206 (the axis that represents the middle of the wearer's hip when worn). It is noted that loop type fastening elements 201 and 203 may merely be disposed on or form a portion of the front region 31a, to which the first hook-type fastening elements 202 and 204 may be fastened with. Improving access to the fastening components 200 by orienting them such that they are in the front region 31a when joined may make opening and refastening of the pant 10 significantly easier for a caregiver and allow front waist region to front region 31a fastening, making the pant 10 changing or pant 10 checking process easier for the caregiver when the wearer is standing in front of the caregiver (e.g., face-to-face) or when the wearer is laying on his or her back. In addition, fastening of the fastening components 200 in the front region 31a of a pant 10 or diaper is also familiar to the caregiver since this is similar to tape-style diapers.

The ability to open and refasten the pants offers convenience to the caregiver. For instance, it might be more convenient to apply the pants as a traditional tape-style diaper when away from home or when it is inconvenient to remove the clothing and/or shoes of the wearer. Because it is difficult to predict when the wearer will need to be changed and, therefore, when a particular mode of application will be needed, it would be beneficial to provide a pant that is adaptable to being applied either as a traditional tape-style diaper or as a disposable training pant. In addition, a product that may be applied like a traditional tape-style diaper or a disposable training pant also permits inspection of the interior of the product without having to slide the product down the legs of the wearer. The pants of the present disclosure provide dual functionality with regard to application and removal while enabling the easy wrapping up and disposal of the used pants.

In various embodiments, each of the fastening components 200 may be joined directly or indirectly to the pant 10 by any suitable methods, such as adhesive bonding, sonic bonding, pressure bonding, thermal bonding or combinations thereof, for example. Some suitable examples of fastening systems and/or the fastening components 200 are discussed in U.S. Pat. Nos. 3,848,594, 4,662,875, 4,846,815, 4,894,060, 4,946,527, 5,151,092, 5,221,274, 6,251,097, 6,669,618, 6,432,098, 7,101,359, and 7,407,468.

Figure 7:
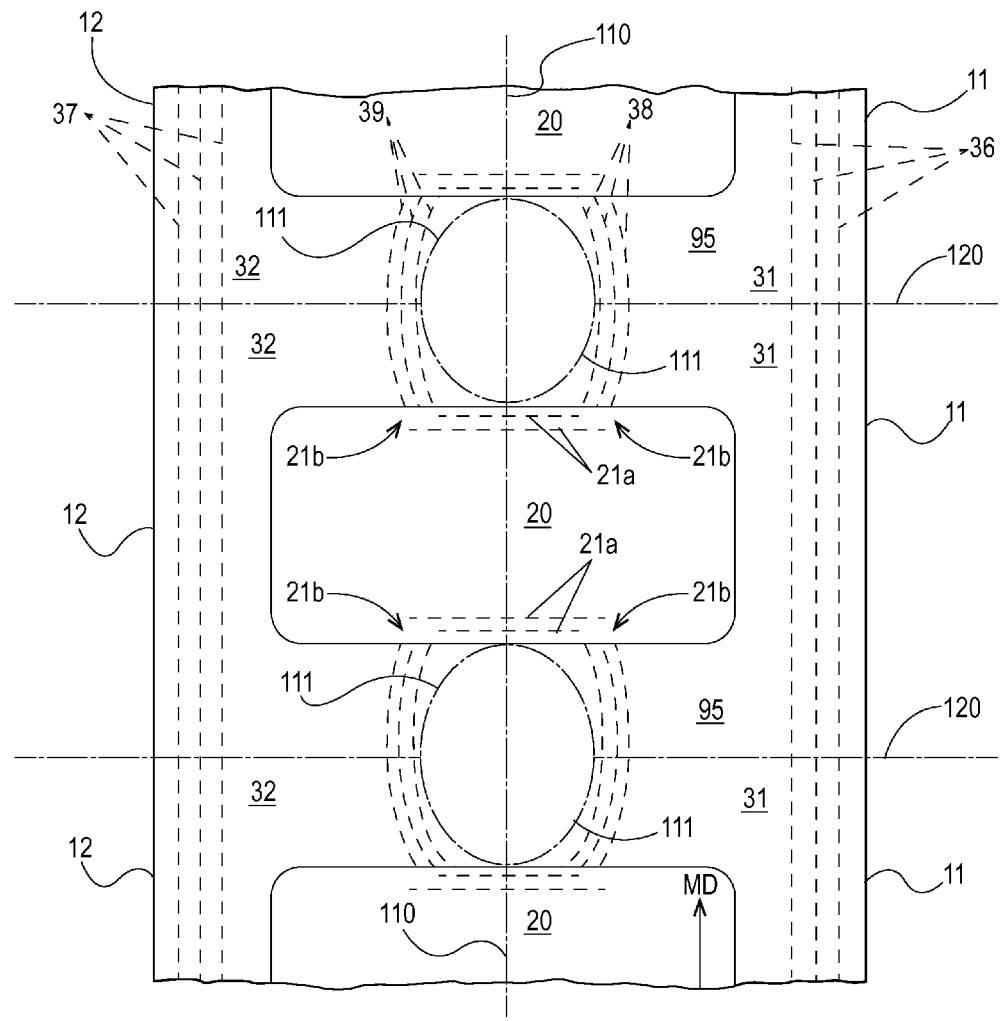
FIG. 7 is a plan view of a multilayer web and applied chassis structures illustrating a method for manufacturing pant structures.
Figure 12:
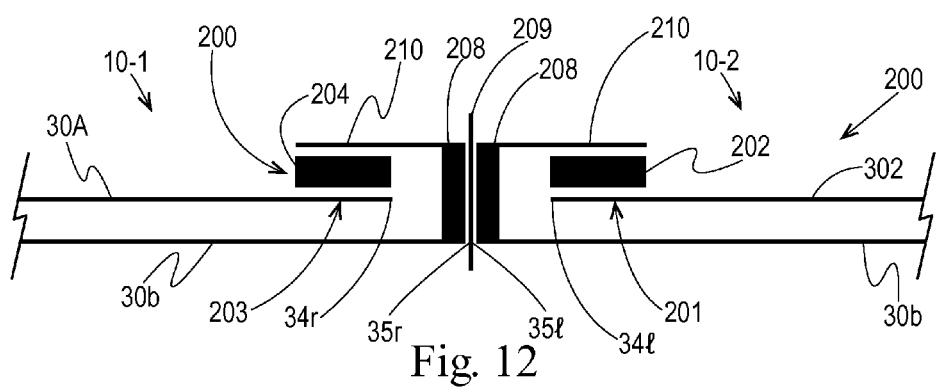
FIGS. 12-17 are simplified, schematic cross-section views of portions of a multilayer web comprising fastening components.

FIG. 12 illustrates the formation of two articles folded over a longitudinal axis (e.g., 110 in FIGS. 2 and 7) to form a pants, pant 10-1 and pant 10-2, wherein only a portion of each is shown. In this embodiment, which is only one embodiment of the present disclosure, each of the pants 10-1 and 10-2 comprise front and rear elasticized belts 30a and 30b disposed in the front and rear regions 31a and 32a, respectively. And, each of the pants 10-1 and 10-2 comprise rear belts 30b that extend from a first side edge 35r and 35l, respectively, to a laterally opposing second side edges (not shown) and form portions of laterally opposing permanent side edge seams 208. Also for each of the pants 10-1 and 10-2, the front belts 30a extend from adjacent a first side edges 34r and 34l, respectively, to an area adjacent the opposing second side edges (not shown) and do not form a portion of the laterally opposing permanent side edge seams 208. The pants 10-1 and 10-2 further comprise fastening tab members 210 disposed outwardly of the front belts 30*a*. The fastening tab members 210 comprise first and second fastening elements 202 and 204 disposed on the interior surface of the fastening tab member 210 disposed between the fastening tab member 210 and the front belts 30*a* and refastenably engaged with the front elasticized belts 30*a*. The fastening tab member 210 forms a portion of the permanent side edge seams 208 and is joined to the rear belts 30*b* at the side edge seam 208.

In an alternative embodiment of the present disclosure (not shown) different from but related to the embodiment of FIG. 12, the front belts extend from first side edges of the article to a laterally opposing second side edges of the articles and form a portion of laterally opposing permanent side edge seams. The rear belts extend from adjacent a first side edge of the article laterally to an area adjacent the opposing second side edge of the articles and do not form a portion of the laterally opposing permanent side edge seams. The articles further comprise fastening tab members disposed outwardly of the rear belt. The fastening tab members comprise first fastening elements disposed on the interior surface of the fastening tab members, between the fastening tab members and the rear belts and refastenably engaged with the rear elasticized belts. The fastening tab members form a portion of the permanent side edge seams and are joined to the front belts at the side edge seams. The fastening components may comprise second fastening elements formed as part of (i.e., integral) or disposed on the rear elasticized belts.

Figure 13:
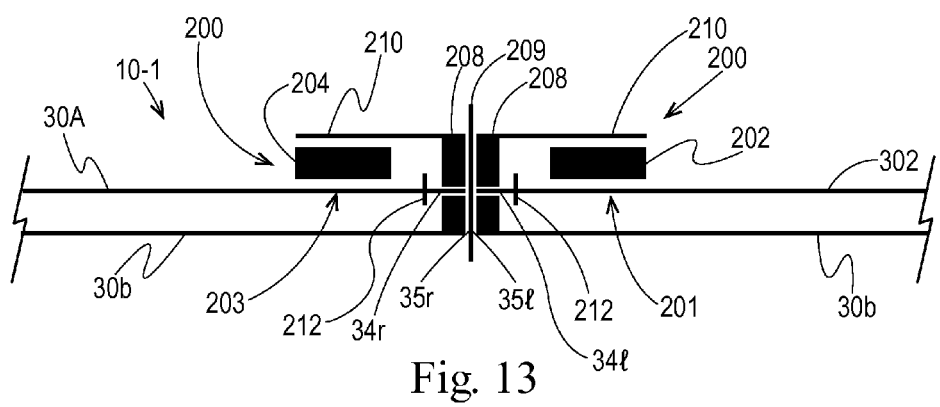

FIG. 13 illustrates the formation of two articles folded over a longitudinal axis (e.g., no in FIGS. 2 and 7) to form a pants, pant 10-1 and pant 10-2, wherein only a portion of each is shown. In this embodiment, which is only one embodiment of the present disclosure, each of the pants 10-1 and 10-2 comprise front and rear elasticized belts 30*a* and 30*b* disposed in the front and rear waist regions 31*a* and 32*a*, respectively. And, each of the pants 10-1 and 10-2 comprise rear belts 30*b* that extend from a first side edge 35*r* and 35*l*, respectively, to a laterally opposing second side edges (not shown) and form portions of laterally opposing permanent side edge seams 208. Also for each of the pants 10-1 and 10-2, the front belts 30*a* extend from adjacent a first side edges 34*r* and 34*l*, respectively, to an area adjacent the opposing second side edges (not shown) and also form a portion of the laterally opposing permanent side edge seams 208. The pants 10-1 and 10-2 further comprise fastening tab members 210 disposed outwardly of the front belts 30*a*. The fastening tab members 210 comprise first and second fastening elements 202 and 204 disposed on the interior surface of the fastening tab member 210 disposed between the fastening tab member 210 and the front belts 30*a* and refastenably engaged with the front elasticized belts 30*a*. The fastening tab member 210 forms a portion of the permanent side edge seams 208 and is joined to the rear belts 30*b* at the side edge seam 208. This embodiment also comprises a tear lines 212 disposed between the side edge seams 34*r* and 34*l* and the first fastening elements 204 and 202. To open the article a user would first unfasten the first fastening element (e.g., 204) from the second fastening element (e.g., 203) and then tear the front belt 30*a* along the tear line 212. To refasten the user would simply refasten the first fastening element (e.g., 202) to the second fastening element (e.g., 201) in the front region 31*a*.

In an alternative embodiment of the present disclosure (not shown) different from but related to the embodiment of FIG. 13, the absorbent articles comprise front and rear elasticized belts disposed in the front and rear regions of the article, respectively. The rear belts extend from first side edges of the articles to laterally opposing second side edges of the articles and form portions of laterally opposing permanent side edge seams. The front belts extend from first side edges of the articles to laterally opposing second side edges of the articles and form portions of laterally opposing permanent side edge seams. The articles further comprise fastening tab members disposed outwardly of the rear belts. The fastening tab members comprise first fastening elements disposed on interior surfaces of the fastening tab members disposed between the fastening tab members and the rear belts and refastenably engage with the second fastening elements or rear elasticized belts. The fastening tab members form portions of the permanent side edge seams and are joined to the front and rear belts at the side edge seams. The fastening components may comprise second fastening elements formed in or disposed on the rear elasticized belts. This embodiment also comprises tear lines (which may be in the form of perforations or weaknesses designed into the substrate) disposed between the side edge seams and the first fastening elements. To open the articles a user would first unfasten the first fastening elements from the second fastening elements and then tear the rear belts along the tear lines. To refasten the user would simply refasten the first fastening elements to the second fastening elements in the rear regions.

Figure 14:
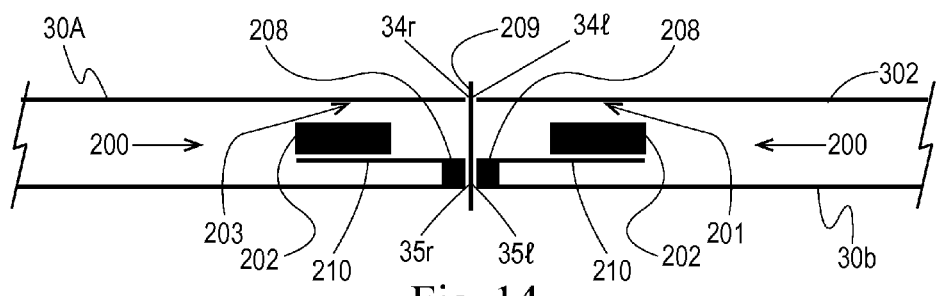

FIG. 14 illustrates the formation of two articles folded over a longitudinal axis (e.g., no in FIGS. 2 and 7) to form a pants, pant 10-1 and pant 10-2, wherein only a portion of each is shown. In this embodiment, which is only one embodiment of the present disclosure, each of the pants 10-1 and 10-2 comprise front and rear elasticized belts 30*a* and 30*b* disposed in the front and rear regions 31*a* and 32*a* of the article 10, respectively. And, each of the pants 10-1 and 10-2 comprise rear belts 30*b* that extend from a first side edge 35*r* and 35*l*, respectively, to a laterally opposing second side edges (not shown) and form portions of laterally opposing permanent side edge seams 208. Also for each of the pants 10-1 and 10-2, the front belts 30*a* extend from adjacent a first side edges 34*r* and 34*l*, respectively, to an area adjacent the opposing second side edges (not shown) and do not form a portion of the laterally opposing permanent side edge seams 208. The pants 10-1 and 10-2 further comprise fastening tab members 210 disposed inwardly of the front belts 30*a*, but outwardly of the rear belts 30*b*, such that they are between the front and rear belts 30*a* and 30*b*. The fastening tab members 210 comprise first and second fastening elements 202 and 204 disposed on the exterior surface of the fastening tab member 210 disposed between the fastening tab member 210 and the front belts 30*a* and refastenably engaged with the front elasticized belts 30*a*. The fastening tab member 210 forms a portion of the permanent side edge seams 208 and is joined to the rear belts 30*b* at the side edge seam 208.

In an alternative embodiment of the present disclosure (not shown) different from but related to the embodiment of FIG. 14, the absorbent articles comprise front and rear elasticized belts disposed in the front and rear regions of the articles, respectively. The front belts extend from first side edges of the article to laterally opposing second side edges of the articles and form portions of laterally opposing permanent side edge seams. The rear belts extend from a first side edges of the articles to a laterally opposing second side edges of the articles, but do not form portions of laterally opposing permanent side edge seams. The articles further comprise fastening tab members disposed inwardly of the rear belts. The fastening tab members comprise first fastening elements disposed on the exterior surfaces of the fastening tab members disposed between the fastening tab members and the rear belts and refastenably engaged with the front elasticized belts. The fastening tab members form portions of the permanent side edge seams and are joined to the front belts at the permanent side edge seams. The fastening components may comprise second fastening elements formed in or disposed on the rear elasticized belts.

Figure 15:
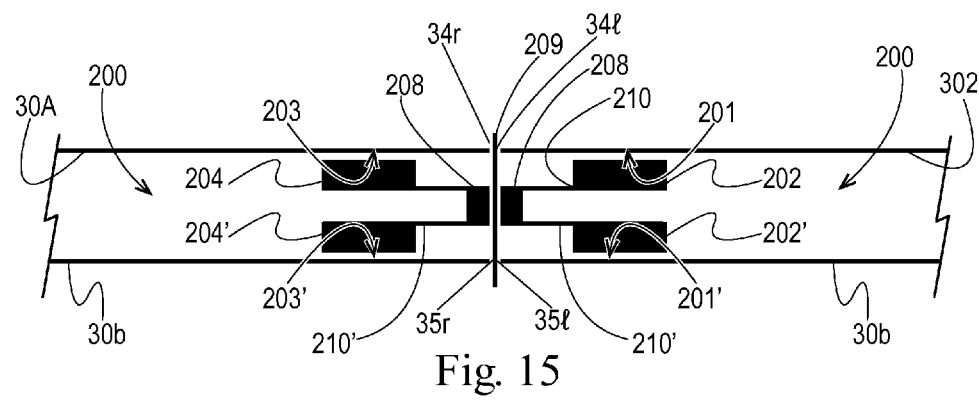

FIG. 15 illustrates the formation of two articles folded over a longitudinal axis (e.g., no in FIGS. 2 and 7) to form a pants, pant 10-1 and pant 10-2, wherein only a portion of each is shown. In this embodiment, which is only one embodiment of the present disclosure, each of the pants 10-1 and 10-2 comprise front and rear elasticized belts 30a and 30b disposed in the front and rear regions 31a and 32a, respectively. And, each of the pants 10-1 and 10-2 comprise rear belts 30b that extend from a first side edge 35r and 35l, respectively, to a laterally opposing second side edges (not shown), but do not form portions of laterally opposing permanent side edge seams 208. Also for each of the pants 10-1 and 10-2, the front belts 30a extend from adjacent a first side edges 34r and 34l, respectively, to an area adjacent the opposing second side edges (not shown), but do not form a portion of the laterally opposing permanent side edge seams 208. The pants 10-1 and 10-2 further comprise fastening tab members 210 and 210' disposed between the front and rear belts 30a and 30b. The fastening tab members 210 and 210' comprise first and second fastening elements 202, 204 and 202', 204' disposed between the fastening tab members 210 and 210' and the front and rear belts 30a and 30b. The fastening tab members 210 and 210' form portions of the permanent side edge seams 208, but are not joined to the front or rear belts 30a and 30b at the side edge seams 208. The fastening components 200 may comprise second fastening elements 201, 203, and 201', 203' formed in or disposed on the respective elasticized belts. The first fastening elements 202, 204 and 202', 204' and the second fastening elements 201, 203, and 201', 203' may be refastenably connected.

Figure 16:
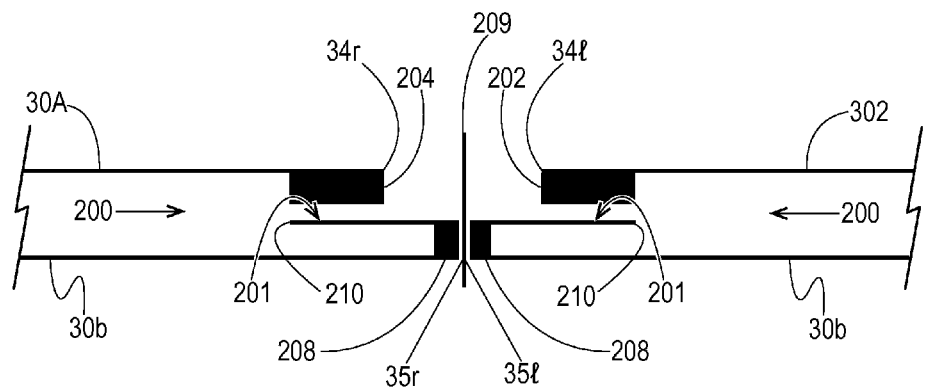

FIG. 16 illustrates the formation of two articles folded over a longitudinal axis (e.g., no in FIGS. 2 and 7) to form a pants, pant 10-1 and pant 10-2, wherein only a portion of each is shown. In this embodiment, which is only one embodiment of the present disclosure, each of the pants 10-1 and 10-2 comprise front and rear elasticized belts 30a and 30b disposed in the front and rear regions 31a and 32a, respectively. And, each of the pants 10-1 and 10-2 comprise rear belts 30b that extend from a first side edge 35r and 35l, respectively, to a laterally opposing second side edges (not shown) and form portions of laterally opposing permanent side edge seams 208. Also for each of the pants 10-1 and 10-2, the front belts 30a extend from adjacent a first side edges 34r and 34l, respectively, to an area adjacent the opposing second side edges (not shown) and do not form a portion of the laterally opposing permanent side edge seams 208. In this embodiment, first side edges 34r and 34l are adjacent edges of fastening elements 202 and 204. The articles further comprise fastening tab members 210 disposed inwardly of and attached to the rear belts 30b forming portions of the permanent side seams 208. The articles also comprise first fastening elements disposed on the interior surfaces of the front belts 30a and disposed between the fastening tab members 210 and the front belts 30a and refastenably engaged with the fastening tab members 210. The fastening components 200 may comprise second fastening elements 201 and 203 formed in or disposed on the fastening tab members 210.

In an alternative embodiment of the present disclosure (not shown) different from but related to the embodiment of FIG. 16, the absorbent articles comprise front and rear elasticized belts disposed in the front and rear regions of the article, respectively. The front belts extends from first side edges of the articles to a laterally opposing second side edges of the article and form portions of laterally opposing permanent side edge seams. The rear belts extend from adjacent first side edges of the articles to adjacent laterally opposing second side edges of the articles, but do not form portions of laterally opposing permanent side edge seams. The articles further comprise fastening tab members disposed inwardly of and attached to the front belt forming portions of the permanent side seams. The articles also comprise first fastening element disposed on the interior surface of the rear belts and disposed between the fastening tab members and the rear belts and refastenably engage with the fastening tab members. The fastening component may comprise second fastening elements formed in or disposed on the fastening tab members.

Figure 17:
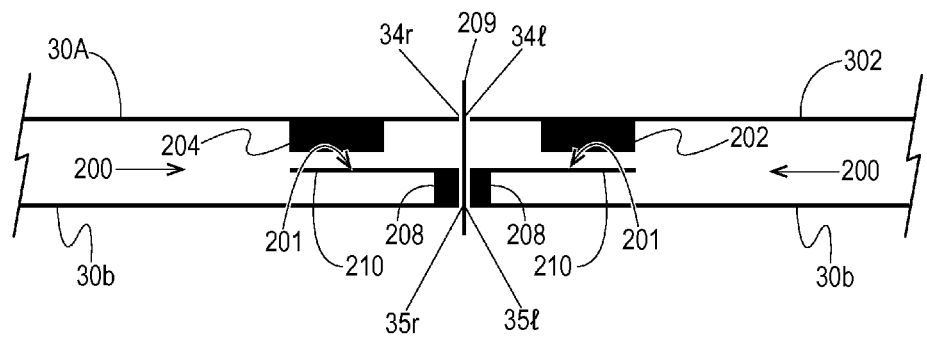

FIG. 17 illustrates the formation of two articles folded over a longitudinal axis (e.g., no in FIGS. 2 and 7) to form a pants, pant 10-1 and pant 10-2, wherein only a portion of each is shown. In this embodiment, which is only one embodiment of the present disclosure, each of the pants 10-1 and 10-2 comprise front and rear elasticized belts 30a and 30b disposed in the front and rear regions 31a and 32a, respectively. And, each of the pants 10-1 and 10-2 comprise rear belts 30b that extend from a first side edge 35r and 35l, respectively, to a laterally opposing second side edges (not shown) and form portions of laterally opposing permanent side edge seams 208. Also, for each of the pants 10-1 and 10-2, the front belts 30a extend from adjacent a first side edges 34r and 34l, respectively, to an area adjacent the opposing second side edges (not shown) and do not form a portion of the laterally opposing permanent side edge seams 208. In this embodiment, first side edges 34r and 34l are spaced apart and adjacent to each other. The articles further comprise fastening tab members 210 disposed inwardly of and attached to the rear belts 30b forming portions of the permanent side seams 208. The articles also comprise first fastening elements disposed on the interior surfaces of the front belts 30a and disposed between the fastening tab members 210 and the front belts 30a and refastenably engaged with the fastening tab members 210. The fastening components 200 may comprise second fastening elements 201 and 203 formed in or disposed on the fastening tab members 210.

In an alternative embodiment of the present disclosure (not shown) different from but related to the embodiment of FIG. 17, the absorbent articles comprise front and rear elasticized belts disposed in the front and rear regions of the articles, respectively. The front belts extends from first side edges of the article to a laterally opposing second side edges of the articles and form portions of laterally opposing permanent side edge seams. The rear belts extend from a first side edge of the article to a laterally opposing second side edges of the article, but do not form portions of laterally opposing permanent side edge seams. The articles further comprise fastening tab members disposed inwardly of and attached to the front belts forming portions of the permanent side seams. The articles also comprise first fastening elements disposed on the interior surface of the rear belts and disposed between the fastening tab members and the rear belts and are refastenably engaged with the fastening tab members. The fastening components may comprise second fastening elements formed in or disposed on the fastening tab member.

Figure 10A:
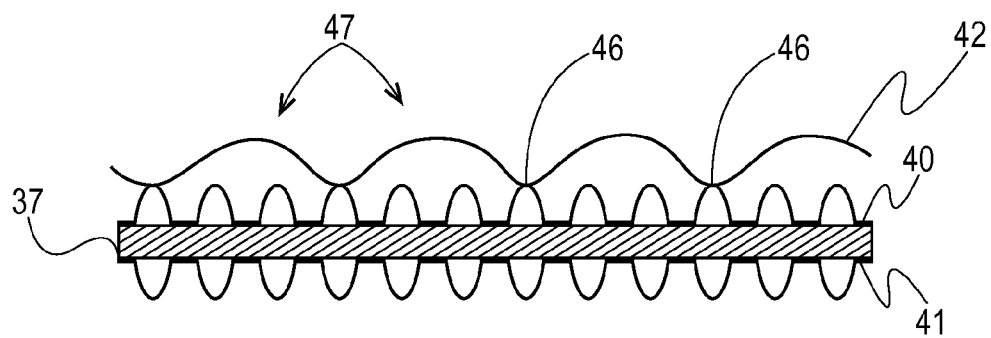
FIGS. 10A-10C are cross-sections similar to that of FIG. 9, but including a third layer and showing examples in which a third layer may be included and attached in an elasticized multilayer web structure and imparted with differing patterns of shirrs.
Figure 10B:
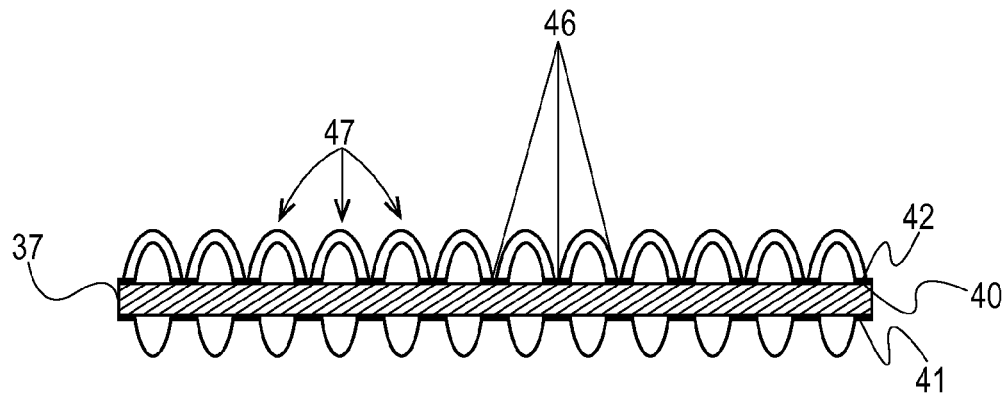
Figure 10C:
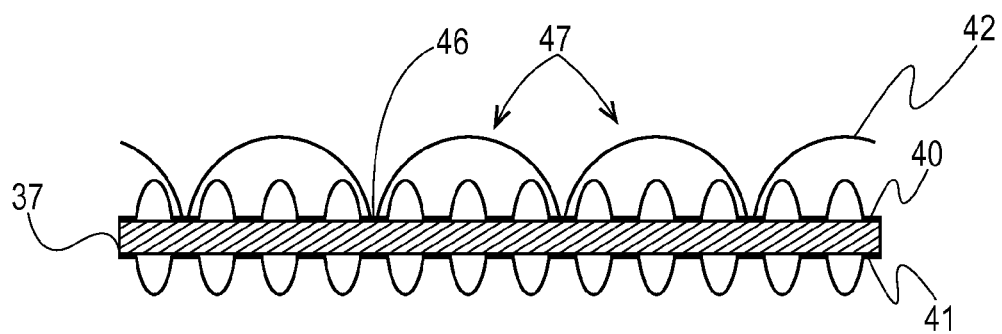

For each of the embodiments illustrated by FIGS. 12-17, as well as the disclosed alternate embodiments of these Figs., it should be understood that the belts 30a and 30b may be formed in accordance with FIGS. 3A-4K as disclosed herein above, as well as in accordance with the disclosure of U.S. 61/646,999, filed on May 15, 2012. And, further, that the methodologies disclosed by FIGS. 5A-8 may be employed, and thus, may enjoy the texture disclosed by FIGS. 9-10C.

Further methods of manufacture and the resulting texture as disclosed by U.S. Ser. Nos. 61/647,061, 61/647,071, 61/647,078, each filed on May 15, 2012, may be used, as well. And, the stress, strain, and spacing of the belt elastics may be done as disclosed in U.S. Ser. No. 61/598,012, filed Feb. 13, 2012.

Also, for each of the embodiments illustrated by FIGS. 12-17, as well as the disclosed alternate embodiments of these Figs., it should be understood that these articles may comprise the cuffs disclosed in U.S. Ser. No. 13/457,521, filed Apr. 27, 2012, and may have graphics in accordance with U.S. Ser. Nos. 61/646,953 and 61/646,979, each filed on May 15, 2012. And, it may be desirable to use the hot air seaming processes, as well as the article forming processes disclosed in U.S. Pat. No. 6,248,195 and U.S. Ser. Nos. 12/795,021, 13/401,907, and 13/402,056 for seaming and forming the refastenable pants disclosed in each of the embodiments illustrated by FIGS. 12-17, as well as the disclosed alternate embodiments of these Figs. as these embodiments are particularly good for producing at high manufacturing speeds up to and exceeding of 1000 articles per minute due to their simplicity. The majority of the article elements including elastic elements are formed continuously in the machine direction. In addition, such a process enables introduction and bonding of refastenable elements to these continuous machine direction sub structures at high speed while maintaining accuracy of placement and ensuring integrity which is key to the products functionality and appearance.

With regard to processing, each of the embodiments illustrated by FIGS. 12-17, as well as the disclosed alternate embodiments of these Figs., offer the advantage of not needing to fold the fastener tab member and/or fastening tab elements. And, because these embodiments offer a permanent side seam, thinner materials can be used for the fastening component. In addition, the simplicity of the design even enables elastomeric materials to be used for the fastening components including the fastening tab members.

All patents and patent applications (including any patents which issue thereon) referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." All documents cited in the Detailed Description of the Invention are, in relevant part, incorporated herein by reference; the citation of any document is not to be construed as an admission that it is prior art with respect to the present disclosure. To the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is, therefore, intended that the scope of the invention is limited only by the appended claims and equivalents thereof.

What is claimed is:

1. An absorbent article comprising:
   a front belt web having an inner wearer-facing surface and an outer garment-facing surface;
   a back belt web;
   first and second fastening tab members;
   first and second fastening elements joined to the first and second fastening tab members, respectively;
   wherein the first fastening tab member is directly joined to a first lateral edge of the back belt web to form a first permanent side seam, and wherein the second fastening tab member is directly joined to a second lateral edge of the back belt web to form a second permanent side seam;
   wherein the first and second fastening elements are hook-type elements and are refastenably engaged with the inner surface of the front belt web:
   wherein the article is packaged in refastenably closed form wherein the first and second fastening tab members are not folded;
   and wherein a first portion of the front belt web overlaps the first permanent side seam and a second portion of the front belt web overlaps the second permanent side seam.

2. The article of claim 1, wherein the first and second fastening elements engage with discrete third and fourth fastening elements attached to the front belt web.

3. The article of claim 1, wherein the first and second fastening tab members are directly and permanently joined to the back belt web, but not the front belt web.

4. The article of claim 1, wherein at least one of the front and back belt webs comprise tear lines.

5. The article of claim 1, wherein the first and second fastening tab members are refastenably joined to the front belt web via the first fastening elements.

6. The article of claim 5, wherein the first and second fastening elements engage into an inner nonwoven layer of the front belt web.

7. The article of claim 1, wherein the first and second fastening elements are not folded.

8. The article of claim 1, wherein the front belt web comprises an inner front belt layer and a portion of an outer cover.

9. The article of claim 8, wherein the back belt web comprises an inner back belt layer and a portion of the outer cover.

10. The article of claim 1, wherein the front and back belt webs are joined to a central chassis.

11. The article of claim 1, wherein the front and back belt webs comprise curved elastic strands adjacent to a leg opening.

* * * * *